(12) United States Patent
Stanley-Marbell et al.

(10) Patent No.: US 10,539,419 B2
(45) Date of Patent: Jan. 21, 2020

(54) METHOD AND APPARATUS FOR REDUCING SENSOR POWER DISSIPATION

(71) Applicant: Massachusetts Institute of Technology, Cambridge, MA (US)

(72) Inventors: Phillip Stanley-Marbell, Boston, MA (US); Martin C. Rinard, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 318 days.

(21) Appl. No.: 15/596,568

(22) Filed: May 16, 2017

(65) Prior Publication Data
US 2018/0094927 A1 Apr. 5, 2018

Related U.S. Application Data

(60) Provisional application No. 62/337,849, filed on May 17, 2016.

(51) Int. Cl.
*G01C 19/10* (2006.01)
*G01P 15/00* (2006.01)

(52) U.S. Cl.
CPC .............. *G01C 19/10* (2013.01); *G01P 15/00* (2013.01)

(58) Field of Classification Search
CPC ............. B60W 10/18; B60W 2710/18; B60W 2720/106; G01P 15/00; G01P 15/18
See application file for complete search history.

(56) References Cited

U.S. PATENT DOCUMENTS

| | | | | |
|---|---|---|---|---|
| 6,268,794 B1 * | 7/2001 | Tzanev | ................... | B62J 6/005 340/427 |
| 6,330,499 B1 * | 12/2001 | Chou | ................... | G07C 5/008 701/31.4 |
| 9,779,557 B2 * | 10/2017 | Hauser | ................... | G07C 5/008 |
| 2013/0006128 A1 * | 1/2013 | Olde | ................... | A61B 5/0215 600/486 |

OTHER PUBLICATIONS

Phillip Stanley-Marbell and Martin Rinard; Lax: Driver Interfaces for Approximate Sensor Device Access; HotOS XV Kartause Ittingen, Switzerland, May 18, 2015.
Phillip Stanley-Marbell and Martin Rinard; Lax: Driver Interfaces for Approximate Sensor Device Access slide presentation; HotOS XV Kartause Ittingen, Switzerland, May 18, 2015.

* cited by examiner

*Primary Examiner* — Elias Desta
(74) *Attorney, Agent, or Firm* — Peter A. Nieves; Sheehan Phinney Bass & Green PA

(57) ABSTRACT

A sensor produces the sensor data for a sensor data consumer. A facility receives a sensor profile of the sensor indicating a relationship between a sensor parameter operating range and a deviation of the sensor data as a result of scaling one or more sensor parameters. The facility receives a tolerance profile of the sensor data consumer indicating a tolerable degree of deviation of the sensor data and scales a parameter of the sensor according to the tolerance profile. The scaling reduces a power dissipation level of the sensor.

17 Claims, 8 Drawing Sheets

METHOD AND APPARATUS FOR REDUCING SENSOR POWER DISSIPATION

CROSS-REFERENCE TO RELATED APPLICATIONS

This application claims the benefit of U.S. Provisional Patent Application Ser. No. 62/337,849, filed May 17, 2016, entitled "Lax: Driver Interfaces for Appropriate Sensor Device Access," which is incorporated by reference herein in its entirety.

GOVERNMENT LICENSE RIGHTS

This invention was made with Government support under Contract No. FA8650-15-C-7564 awarded by the U.S. Air Force. The Government has certain rights in the invention.

FIELD OF THE INVENTION

The present invention relates to electronic circuitry, and more particularly, is related to electronic sensors.

BACKGROUND OF THE INVENTION

Sensors are becoming the dominant source of power dissipation in environment monitoring, wearable, and health tracking systems. Embedded sensor platforms may dissipate most of their energy in accessing sensor integrated circuits such as gyroscopes. Therefore, there is a need to address power dissipation in sensor systems.

SUMMARY OF THE INVENTION

Embodiments of the present invention provide a method and apparatus for reducing sensor power dissipation. Briefly described, the present invention is directed to a sensor producing sensor data for a sensor data consumer. A facility receives a profile of the sensor indicating a relationship between a sensor parameter operating range and a deviation of the sensor data as a result of scaling one or more sensor parameters. The facility receives a tolerance profile of the sensor data consumer indicating a tolerable degree of deviation of the sensor data and scales a parameter of the sensor according to the tolerance profile. The scaling reduces a power dissipation level of the sensor.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The components in the drawings are not necessarily to scale, emphasis instead being placed upon clearly illustrating the principles of the present invention. The drawings illustrate embodiments of the invention and, together with the description, serve to explain the principles of the invention.

DETAILED DESCRIPTION

Figure 1:
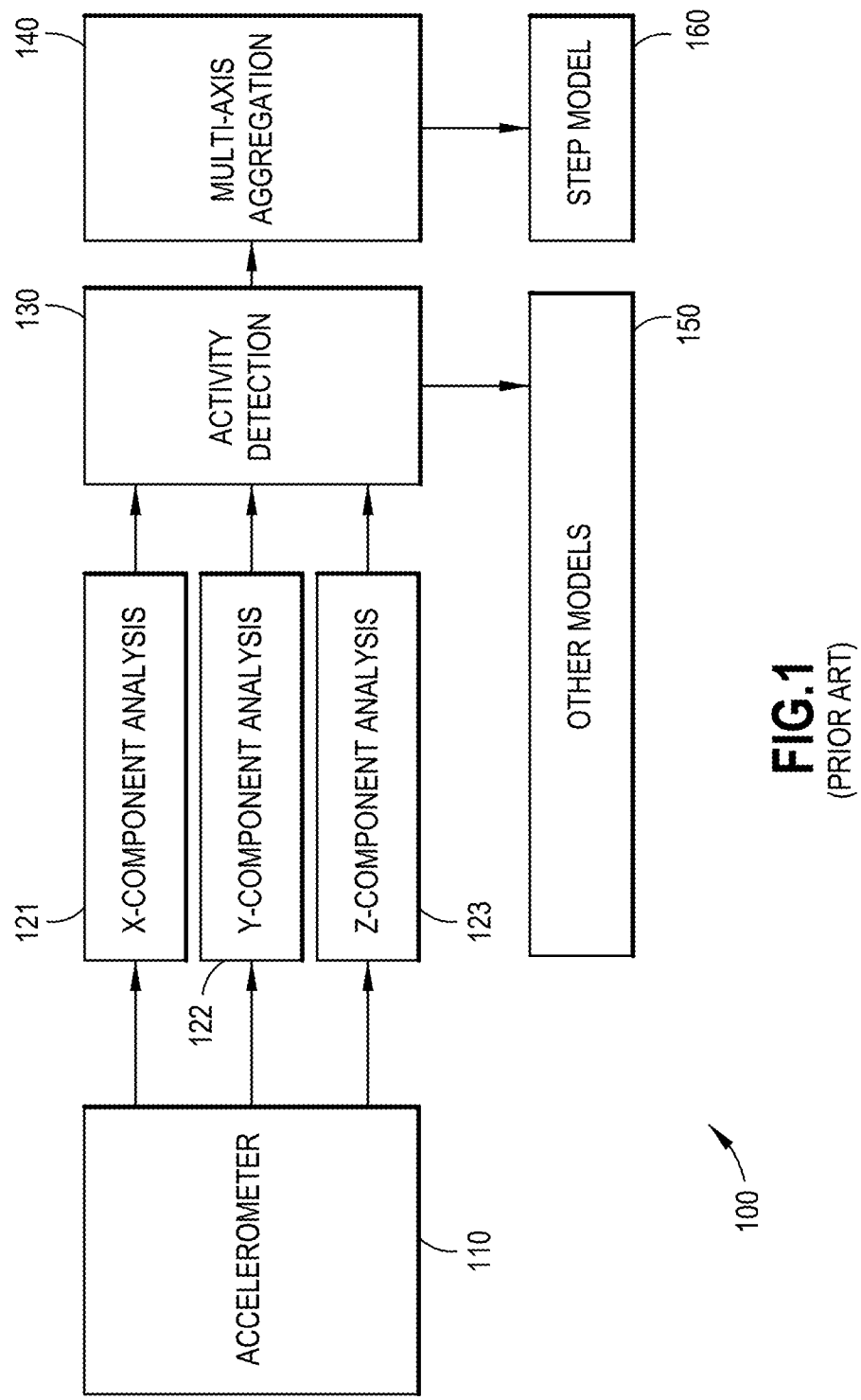
FIG. 1 is a schematic diagram showing a prior art sensing system 100, namely an exemplary pedometer application.

The following definitions are useful for interpreting terms applied to features of the embodiments disclosed herein, and are meant only to define elements within the disclosure.

As used within this disclosure "bare metal" refers to an implementation of embedded components without an operating system or with a minimal and/or stripped down operating system.

As used within this disclosure, "Lax" refers to one or more systems, devices, facilities, and/or methods for leveraging tolerances to deviations in data produced by one or more sensors.

Reference will now be made in detail to embodiments of the present invention for systems, devices, and/or methods for leveraging tolerances to deviations in sensor data, referred to hereinafter as "Lax", examples of which are illustrated in the accompanying drawings. Wherever possible, the same reference numbers are used in the drawings and the description to refer to the same or like parts.

Consumers of data from sensors may often tolerate some amount of deviation (errors) in the retrieved sensor values. Because sensor-equipped devices may be accessed through interfaces provided by system software, exploiting the tolerable error in exchange for improvements in energy efficiency may be achieved for exemplary embodiments of Lax by appropriate system software and hardware support.

Several characteristics make sensors especially amenable to energy savings through approximation. First, sensors are typically stateless so that errors in one sample do not propagate to affect the next sample. Digital computation, in contrast, is typically state based, so that errors in control logic may accumulate over time. Second, sensor interaction is typically transactional, with the obtained values having limited temporal influence. Third, because sensors are primarily analog circuits, they are better able to tolerate approximate computing mechanisms that can lead to catastrophic failures when applied to digital microprocessors. For example, values in the analog signal domain are continuous rather than discrete, and the noise in these values within analog circuit components typically smoothly increases as they are operated at successively lower operating voltages. In digital circuits, by contrast, operation at successively lower operating voltages leads to large discrete errors and abrupt failures. In addition to the challenges of application to digital circuit components, previous sensor approximation techniques have not been adequately controllable, and have lacked an appropriate interface to algorithms to provide approximate sensor access and control.

Exemplary embodiments of Lax presented here provide a device driver abstraction and associated hardware support that exploits opportunities to trade sensor accuracy and reliability for significant energy savings. The exemplary embodiments leverage the insight that in certain phases of their lifetime, the consumers of sensor data, may be able to tolerate some amount of error in retrieved sensor values. Examples of consumers of sensor data may include, for example, algorithms which process sensor data, and humans who consume the overall output of embedded sensor systems.

The exemplary embodiments provide a system that enables sensor data consumers to specify how much error they can tolerate from a sensor. Armed with this specification of acceptable error levels, the exemplary embodiments may then control an electrical interface of the sensor to minimize sensor energy consumption while still delivering acceptable sensor accuracy and reliability. This may be accomplished without changes to the sensor and/or sensor integrated circuits, for example, via a combination of software and external printed circuit board components.

The exemplary embodiments may combine software and hardware support to trade efficiency for accuracy and reliability. The exemplary embodiments provide a system, explained in detail below, that enables sensor device accessors to specify a tolerable degree of imprecision, inaccuracy, and unreliability. For sensors with limited support for modes which trade resolution for access power, the embodiments exploit the extant hardware facilities. Even when sensors do not have existing hardware support for trading precision, accuracy, or reliability for power consumption, many sensors may be operated outside their specified supply voltages, for example by adjusting a voltage regulator controlling a voltage level used to provide power to the sensor. For example, reducing the voltage supplied to a humidity or accelerometer sensor by half may reduce power dissipation by a factor of approximately 4 while only increasing noise output of the sensor by a factor of approximately 1.5. These savings may be significantly larger than the hypothetical savings supposed for future approximate processors and may be achieved without resorting to the complex micro-architectural changes required by, for example, proposed mixed-accuracy processors. Leveraging this provides usable tradeoffs between the reliability of data acquisition, fidelity of data provided, and power dissipation, as described below in detail.

FIG. 1 is a block diagram indicating data flow for a prior art sensing system 100, an exemplary pedometer application, as might be incorporated into popular wearable health-tracking platforms. FIG. 1 shows the data flow from an accelerometer sensor 110 through blocks of the signal processing needed to perform step counting. The accelerometer sensor 110 provides three output signals corresponding to sensed acceleration in three directions for Cartesian coordinates, processed individually by an x-component analysis block 121, a y-component analysis block 122, and a z-component analysis block 123.

The outputs of the component analysis blocks 121, 122, 123 are received by an activity detection block 130, which receives samples from the accelerometer sensor 110 indicating the x-, y-, and z-components of acceleration that may be first low-pass filtered, then processed by an activity detection algorithm. If a motion signature produced by the activity detection indicates walking, these acceleration components are fed into a model for predicting steps from acceleration signatures.

The activity detection block 130 feeds a multi-axis aggregation block 140, and optionally, other modules 150. Examples of other modules 150 include a gait analysis block to analyze aspects of the gait of a person that might be indicative of a disease or injury, or a gesture recognition block for controlling other functionality in a system. The multi-axis aggregation block 140 provides an aggregated output to a step model 160. In general, the prior art sensing system 100 cannot specify how much precision, accuracy, or reliability is required from the accelerometer sensor 110.

Figure 2:
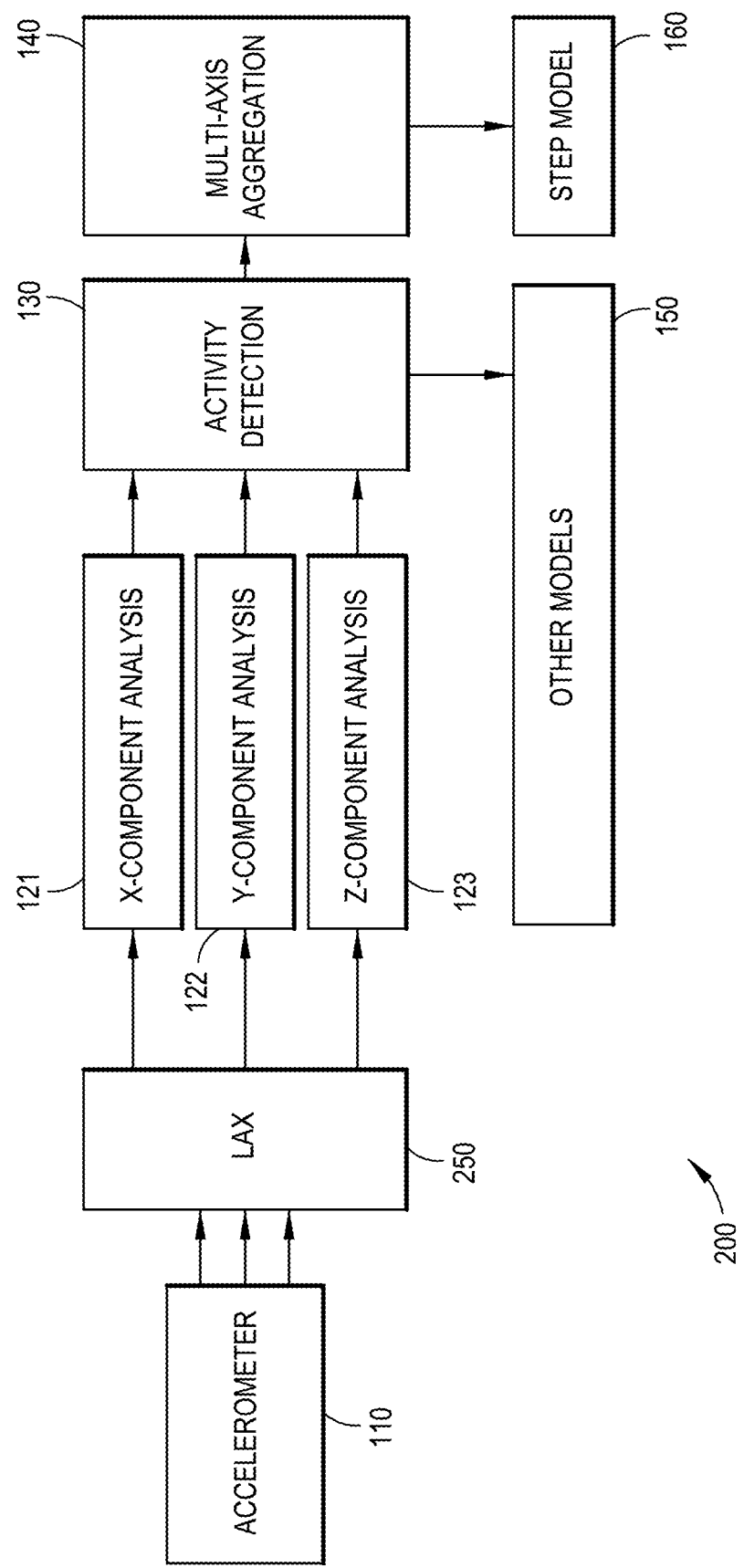
FIG. 2 shows the sensing system of FIG. 1 adapted with a first exemplary embodiment of a system for reducing energy used by sensors while at the same time tolerating deviations in sensor data.

FIG. 2 is a block diagram indicating data flow for a modified sensing system 200 where facilities 250 for Lax have been logically interposed after the accelerometer sensor 110 in the interface to the component analysis blocks 121, 122, 123 (data acquisition blocks).

Figure 6:
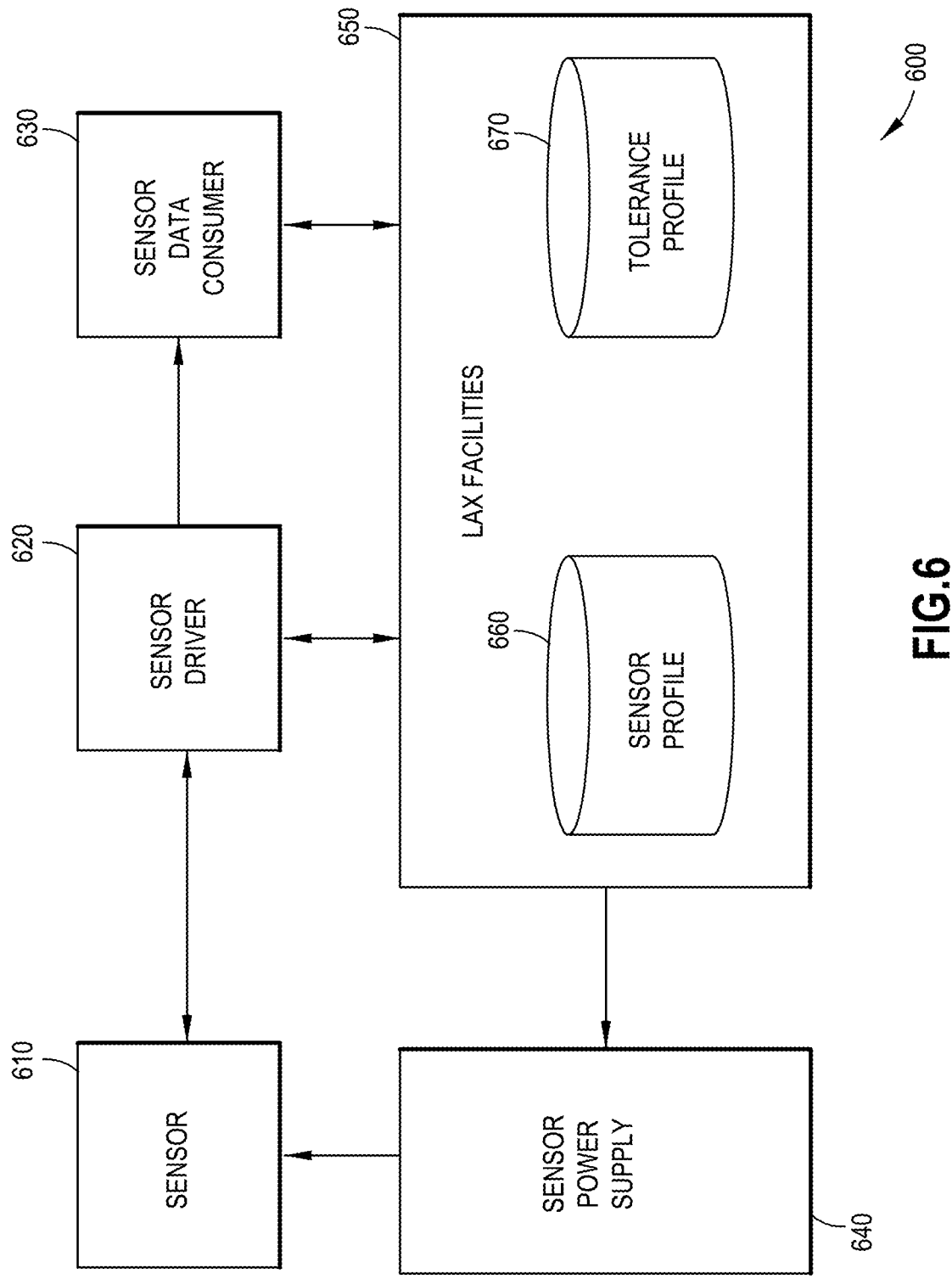
FIG. 6 shows a simplified block diagram of the first exemplary embodiment of a sensor system.

FIG. 6 shows a simplified block diagram 600 of the first exemplary embodiment of a sensor system. The system includes a sensor 610 configured to sense a target parameter and report sensor data indicative of the target parameter. For example, if the sensor 610 is a temperature sensor, the target parameter may be a measured temperature, and if the sensor 610 is a humidity sensor, the target parameter may be a measured humidity.

A sensor driver 620 is configured to communicate with the sensor 610, for example, as a controller that configures operating parameters of the sensor 610. The sensor driver 620 may also receive and/or accumulate data from the sensor 610. The sensor driver 620 may be integral to the sensor 610, or may be external to the sensor 610, implemented in hardware, for example, as a stand-alone driver, or in software or firmware, for example as a module operating on an external device. The sensor driver 620 may function as an intermediary between the sensor 610 and a sensor data consumer 630, as shown in FIG. 6, or, alternatively, the sensor data consumer 630 may receive data directly from the sensor 610.

A sensor power supply 640 may provide power to the sensor 610. The sensor power supply 640 may be integral to the sensor 610, or may be external to the sensor 610. The operation of the sensor power supply 640 may be controlled by the Lax facilities 650 to regulate one or more aspects of power provided to the sensor 610, for example, a voltage level and/or a current level. However, other power parameters may also be controlled, for example, a level of power conditioning and/or filtering that may be used to regulate the consistency of the voltage and/or current provided to the sensor 610. While, in general, the Lax facilities 650 are described herein as modifying operating parameters of the sensor 610 and/or the sensor power supply 640, in alternative embodiments the Lax facilities 650 may instead and/or in addition modify operating parameters of the sensor driver 620 and/or the sensor data consumer 630, such that power savings may be gained from modifications to operation of the sensor driver 620, as well as just the sensor 610 itself. The relationship between sensor parameter modifications and deviations in sensor data may be stored in a sensor profile 660, as described in detail below.

The Lax facilities 650 may be in communication with the sensor data consumer 630, for example, to interact with the sensor data consumer 630 regarding a tolerance profile 670 of the sensor data consumer 630, as described below.

The Lax facilities 650 provides system software interfaces for approximate device access, enabling the specification of one or more types of tolerance to deviations in the sensor data from correct behavior, including, for example, but not limited to latency tolerances, loss or throughput tolerances, and/or value deviation tolerances. The Lax facilities 650 may include both hardware and software components, for example, a processor executing software modules for processing data received from the sensor 610, and the software modules for executing the functionality of the Lax facilities 650.

The block diagram of FIG. 6 is provided to indicate the various functionalities of the system embodiments. However, in alternative embodiments, two or more of the blocks may be combined together, for example, the Lax facilities 650 and the sensor driver 620 may be combined, among other possible combinations.

As used within this document, "latency tolerances" refer to the capacity of an application servicing a sensor to operate correctly if the time between values recovered from a sensor is varied. For example, different applications may tolerate differing latencies in retrieving values from a sensor. This may be exploited by the Lax facilities 650 to reduce the energy required per sensor sample acquisition.

As used herein, "deviation" refers to a difference between output readings of a sensor with and without scaling one or more sensor parameters.

As used herein, "loss tolerances," or "throughput tolerances" refer to the capacity of an application servicing a sensor to operate correctly if one or more collections of data from a sensor is either missed or is inaccurate. When the sensor data consumer 630, for example, algorithms consuming sensor data, can tolerate occasional wholly incorrect or missing samples, knowledge of this tolerance of unreliability may be used to reduce sample acquisition energy.

As used herein, "value deviation tolerances" refer to the capacity of an application servicing a sensor to operate correctly if a value reported by a sensor deviates in terms of accuracy and/or precision from the actual value being measured by the sensor. When the algorithms consuming sensor values can tolerate small deviations from accuracy or precision in sensor readings, this may be exploited to reduce sample acquisition energy.

Other parameters involving trading sensor precision/accuracy for power consumption may include the bit granularity of digital data reported by a sensor, for example, changing a serial bus output of the sensor 610 from 12 bits to 8 bits, and/or smoothing/averaging parameters. For example, the sensor 610 and/or the sensor driver 620 and/or the sensor data consumer 630 may accumulate several sensor readings (samples) over time and calculate an average of the samples before reporting the average as the sensor output. Reducing the number of samples used to calculate the average, or eliminating the averaging function altogether may reduce the power consumption of the sensor system 600, while increasing the noise and/or reducing the accuracy of the sensor data.

The first exemplary embodiment 600 enables driver writers to specify tolerances to one or more of these types of behavioral aberrations. These specifications may then be exploited in existing system architectures, as illustrated in FIG. 3.

Figure 3:
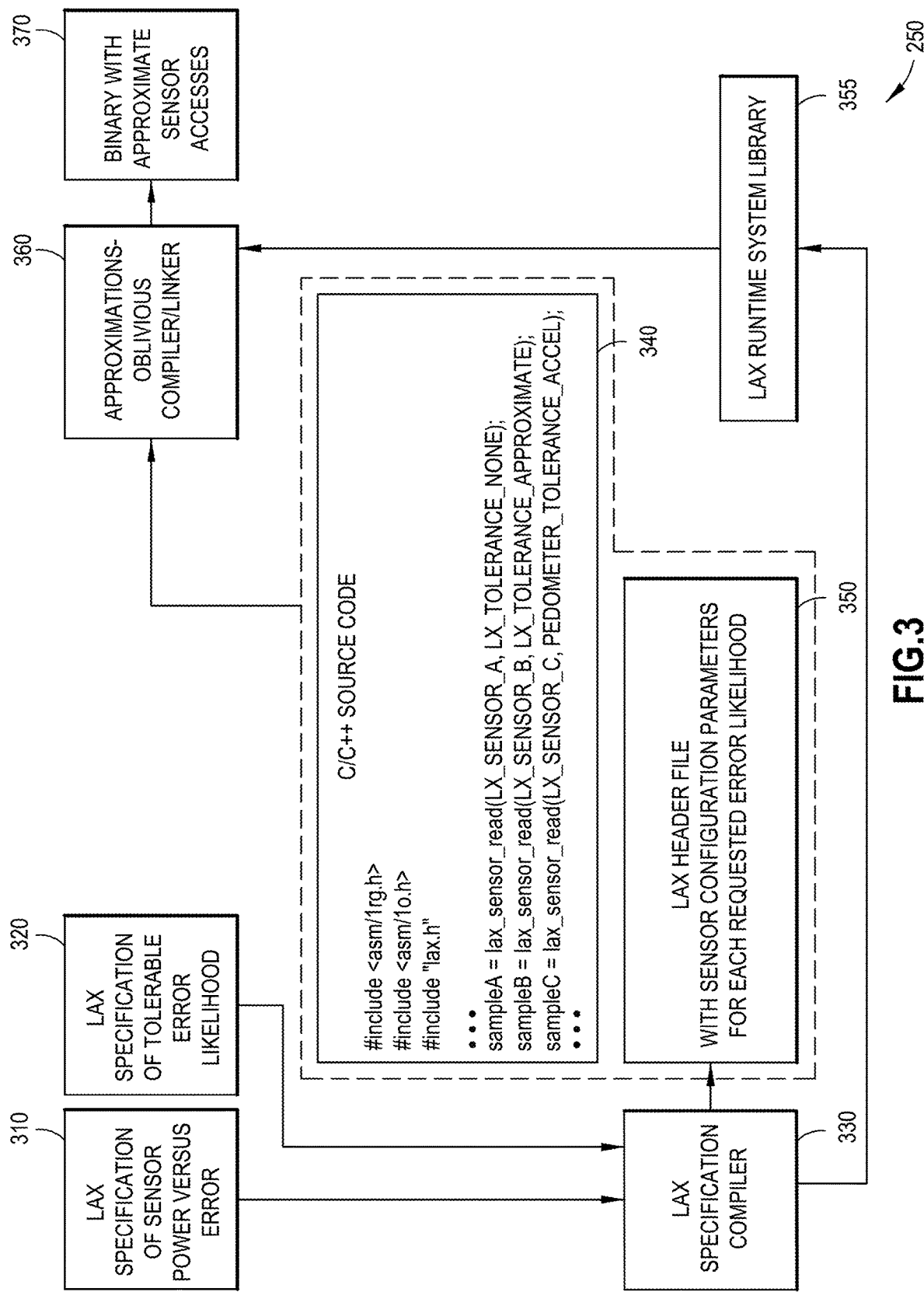
FIG. 3 is a block diagram detailing the first exemplary embodiment of the system for reducing energy used by sensors while at the same time tolerating deviations in sensor data of FIG. 2.

As shown in FIG. 3, software may use Lax primitives to request sensor values (block 340). The amount of inaccuracy, imprecision, and/or unreliability that is tolerable in responses to those requests may be either specified using defaults such as LX_TOLERANCE_NONE, or application-specific tolerances such as PEDOMETER_TOLERANCE_ACCEL. The meaning of these optional constants may be specified explicitly in the tolerable error specification (block 320). The Lax specification compiler 330 combines these with the hardware error characteristics (block 310) to emit source and headers that implement the approximate sensor access (blocks 350, 355).

Tolerances may generally be specified in the context of a given sensor type and may preferably be statically checked because it is possible to specify meaningless, unattainable, or mutually contradictory tolerance specifications. Lax may use a utility for defining tolerances, for example, a small domain-specific language, Slax. Slax captures the latency, loss, and value-deviation tolerances of sensor data acquisition and is thus complementary to interface definition languages which are intended to ease the construction of complete device drivers.

An exemplary set grammar definitions for Slax is shown in Table 1:

TABLE 1

Grammar for Slax

| # | Name | Definition |
|---|---|---|
| 1 | unsignedImm | ::= "0" | "1..9" {"0..9"} . |
| 2 | stringConst | ::= "\"" {Unicode Character} "\"" . |
| 3 | integerConst | ::= ["+" | "−"] unsignedImm . |
| 4 | dRealConst | ::= ("0" | "1..9" {"0..9"}) "." "0..9" {"0..9"} . |
| 5 | eRealConst | ::= (dRealConst | integerConst) ("e" | "E") integerConst . |
| 6 | realConst | ::= dRealConst | eRealConst . |
| 7 | rationalConst | ::= integerConst "/" integerConst . |
| 8 | numConst | ::= integerConst | rationalConst | realConst . |
| 9 | | |
| 10 | slaxSpec | ::= specHead {defn} . |
| 11 | specHead | ::= "specification" ident ";" . |
| 12 | ident | ::= {Unicode Character} . |
| 13 | defn | ::= sensorDefn | toleranceDefn . |
| 14 | sensorDefn | ::= "sensor" ident ["@"numConst units] "=" "{" {sensorStmt} "}". |
| 15 | toleranceDefn | ::= "tolerance" ident "=" "{" {toleranceStmt} "}". |
| 16 | sensorStmt | ::= "provide" "(" eClass ")" "=" "{" cStmt {";" cStmt} "}" . |
| 17 | toleranceStmt | ::= "require" "(" eClass ")" "=" "{" cStmt {";" cStmt} "}" . |
| 18 | eClass | ::= "deviation" | "latency" | "loss" | "throughput" . |
| 19 | cStmt | ::= cmpOp numConst units ":" likelihoodExpr | alwaysExpr . |
| 20 | likelihoodExpr | ::= "likelihood" cmpOp numConst "in" numConst "readings" . |
| 21 | alwaysExpr | ::= "always" cmpOperator numConst . |
| 22 | cmpOp | ::= ">" | ">=" | "<" | "<=" | "==" . |
| 23 | units | ::= "s" | "ms" | "us" | "ns" | "W" | "mW" | "uW" | "nW" | "%" . |
| 24 | | |
| 25 | reservedTokens | ::= "%" | "(" | ")" | ":" | ";" | "<" | "=" | ">" | "always" |

TABLE 1-continued

Grammar for Slax

| | |
|---|---|
| 26 | \| "deviation" \| "in" \| "latency" \| "likelihood" \| "loss" |
| 27 | \| "ms" \| "ns" \| "occurs" \| "provide" \| "readings" |
| 28 | \| "require" \| "s" \| "sensor" \| "specification" |
| 29 | \| "throughput" \| "tolerance" \| "us" \| "{" \| "}" . | and example specifications for an accelerometer are given in Table 2 and Table 3:

TABLE 2

Example Slax specification for sensor

| | |
|---|---|
| 1 | specification AccelerometerSensor; |
| 2 | |
| 3 | sensor PLATFORM_ACCELEROMETER_A @ 1.6V = { |
| 4 | provide (latency) { |
| 5 | > 1 ms : likelihood < 1 in 1E6 readings; |
| 6 | } |
| 7 | provide (deviation) { |
| 8 | > 1% : likelihood < 1 in 1E6 readings; |
| 9 | > 10% : likelihood < 1 in 1E9 readings; |
| 10 | } |
| 11 | provide (loss) { |
| 12 | occurs: likelihood < 1 in 1E6 readings; |
| 13 | } |
| 14 | } |

TABLE 3

Example Slax specification for tolerance

| | |
|---|---|
| 1 | specification PedometerApp; |
| 2 | |
| 3 | tolerance PEDOMETER_TOLERANCE_ACCEL = { |
| 4 | require (deviation) { |
| 5 | > 1% : likelihood < 1 in 1000 readings; |
| 6 | } |
| 7 | require (latency) { |
| 8 | > 1ms : likelihood < 1 in 1000 readings; |
| 9 | } |
| 10 | require (loss) { |
| 11 | occurs : likelihood < 1 in 1000 readings; |
| 12 | } |
| 13 | } |

A Slax specification may include one or more sensor and/or tolerance blocks. The sensor blocks describe the error properties of sensors at various operating points, while the tolerance blocks denote groups of error tolerance settings that are required together at various points in an application.

In practice, a driver may use a Lax-default or driver specified tolerance specification in accessing a given sensor, as illustrated in block 340 of FIG. 3. For example, given the Slax specifications in Table 2 and Table 3, the following C language fragment would employ the configuration implied by the constants PLATFORM_ACCEL_A and PEDOMETER_TOLERANCE_ACCEL:

```
/* Use Lax to achieve lowest power for required accuracy.
*/
    sampleC = lax_sensor_read(PLATFORM_ACCEL_A,
        PEDOMETER_TOLERANCE_ACCEL);
```

The Lax runtime may use the provided tolerance indicator to determine the best device operating point. When integrated into contemporary operating systems, it would then set the properties of the device using, e.g., ioctl( ) or equivalent system calls. The sensor blocks on the other hand are preferably based on hardware characterizations. They would preferably be provided by a hardware platform designer or vendor, but may be overridden by a sensor block of the driver writer.

As shown in Table 4, The energy savings for the exemplary embodiments of Lax may be verified, for example, by performing data integrity measurements at different degrees of power savings for two exemplary sensors:

TABLE 4

| Sensor | Power Dissipation (µW) | Supply Range (V) |
|---|---|---|
| Gyroscope L3G4200D | 18300 | 2.4-3.6 |
| IR Temperature TMP006B | 528 | 2.5-5.5 |

The sensors listed in Table 4, were both targeted at mobile and wearable computing systems and each dissipate more power when active than the processor shown in FIG. 1 when that processor is operating in a low-power active mode. In a typical system, the sensors may be sampled whenever the processor wakes from sleep, consuming a significant portion of overall system energy usage. Under the first embodiment, each sensor may be operated at a range of voltages below their nominal operating points and the types of errors encountered may be characterized. The errors under these conditions may be of two types: (1) sample loss, or erasures (in the information-theoretic sense), where communication with a sensor fails; or (2) value deviations, where values are retrieved from a sensor, but they are different from those that would have been retrieved when operating the sensor at its nominal operating voltage. Where appropriate, such as when the default effect of failures would be to cause existing software that interacts with sensors to witness error conditions, the low-level interface code for interfacing with sensors may be modified for accessing the sensors to recover gracefully from access failures (e.g., replacing assertions with more graceful return status codes). This approach may be used for bare metal embedded implementation. When Lax is integrated into a sophisticated operating system, such changes may still suffice, or may be augmented with techniques such as, for example, micro-reboots, or tools such as Carburizer.

Figure 4:
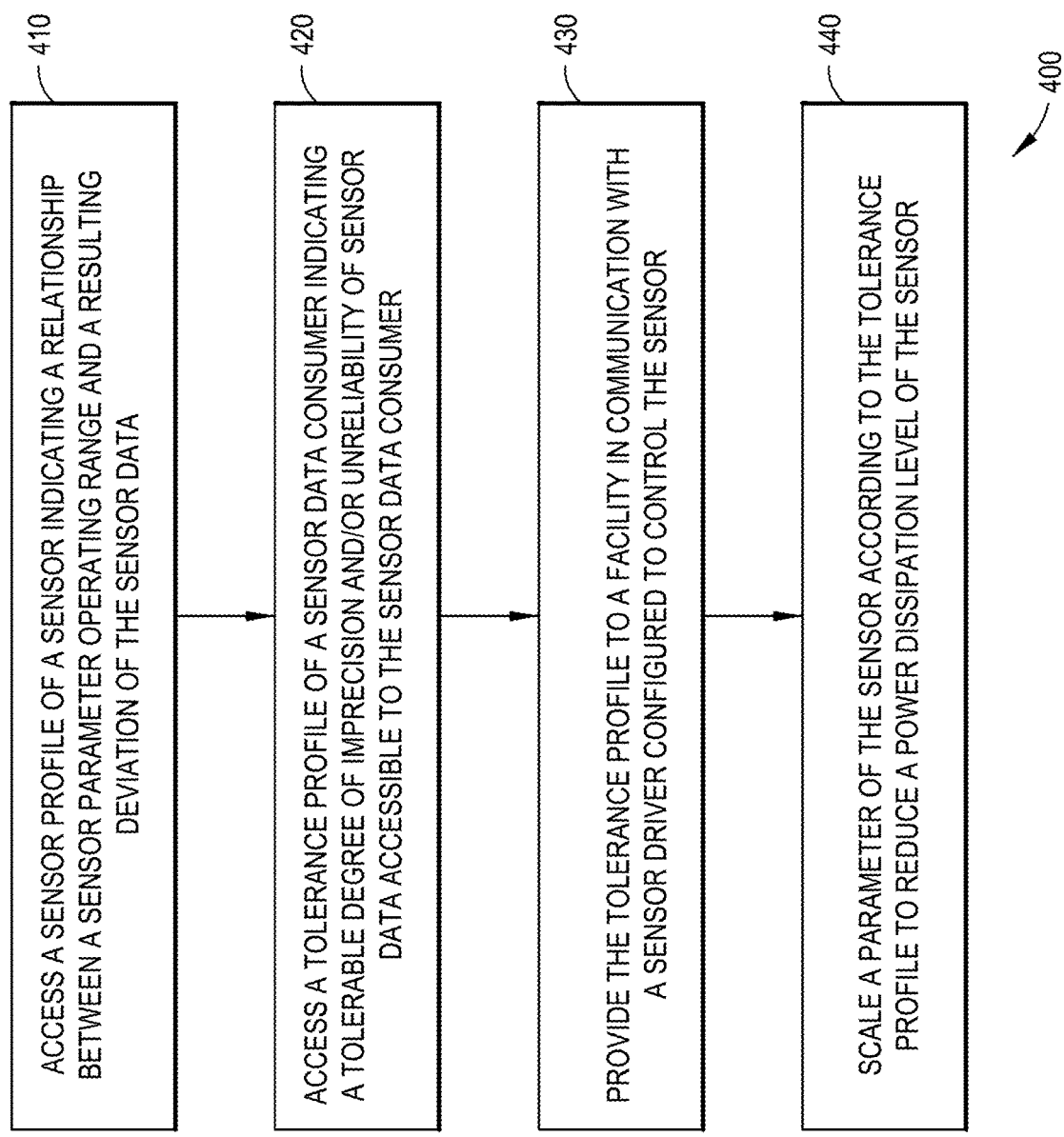
FIG. 4 is a flow chart of a first exemplary process for executing the embodiment shown in FIG. 1.

FIG. 4 is a flowchart of an exemplary method for reducing power in a sensor system. It should be noted that any process descriptions or blocks in flowcharts should be understood as representing modules, segments, portions of code, or steps that include one or more instructions for implementing specific logical functions in the process, and alternative implementations are included within the scope of the present invention in which functions may be executed out of order from that shown or discussed, including substantially concurrently or in reverse order, depending on the functionality involved, as would be understood by those reasonably skilled in the art of the present invention. The blocks of the flowchart 400 are explained with reference to FIG. 6.

A sensor profile 660 indicates deviations such as inaccuracies, imprecisions, latencies, losses, or all of the above, introduced to data produced by a sensor 610 as a result of adjusting one or more operating parameter of the sensor 610. For example, the sensor profile 660 may include deviations produced by operating the sensor 610 at voltages below the specified operating range of the sensor 610. The sensor profile 660 of the sensor 610 indicating a relationship between a sensor parameter operating range and a resulting deviation of the sensor data is accessed, as shown by block 410.

A tolerance profile of a sensor data consumer 630 is accessed indicating a tolerable degree of imprecision, inaccuracy, and/or unreliability of sensor data accessible to the sensor data consumer 630, as shown by block 420. The tolerance profile 670 is provided to a Lax facility 650 in communication with a sensor driver 620 configured to control the sensor, as shown by block 430. A parameter of the sensor 610 is scaled, for example, by the Lax facility 650, according to the tolerance profile to reduce a power dissipation level of the sensor, as shown by block 440.

The sensor profile 660 may be created independently of the first embodiment system 600, and may be provided to the first system embodiment 600 for operation. Alternatively, the Lax facilities 650 may be used to produce the sensor profile 660, for example, by using the sensor 600 and a reference sensor (not shown) operated in close proximity to one another, where the Lax facilities 650 are used to control one or more operating parameters of the sensor 600, while the reference sensor is not adjusted. The Lax facilities 650 may then compare data collected from the sensor 600 with data collected from the reference sensor to determine if and how adjustment of the operating parameter(s) of the sensor 600 results in deviations in data collected from the sensor 600 with respect to data collected from the reference sensor. The sensor profile 660 may be filled in by repeating this process over a range of values for one or more parameters of the sensor 610.

In addition to deviations in data precision, when the sensor 610 is operated outside of specified operating parameters, deviations in the data produced by the sensor 610 may include an offset value. The offset value may scale according to changes in one or more operating parameters of the sensor 610, or the offset value may represent a non-linear deviation. The Lax facilities 650 may be configured to address offsets in different ways described below.

Regarding precision, the sensor 610, for example, a temperature sensor operated within specified operating parameter ranges, may report a temperature accurate to two decimal places with an error range of +/−0.1%, while operating the same temperature outside of specified operating parameter ranges.

Regarding offset, the sensor 610 operated below specified operating parameter ranges may result in reporting data with an error offset. For example, a temperature sensor operated at a voltage level below the specified minimum voltage level may report a temperature level with a known error offset. For instance, at a voltage level 20% below the specified minimum voltage level the sensor may report a temperature level that has an error offset of −12 degrees, so that 12 degrees must be added to the temperature value reported by the sensor to determine the correct temperature. Including such offset information in the sensor profile may allow the Lax facilities 650 to correct the sensor reading by configuring the sensor driver 620 to add the known offset to the received sensor reading. Alternatively, the Lax facilities 650 may alert the sensor data consumer 630 of the offset, so the sensor data consumer 630 may adjust the received sensor data to correct for the offset.

Figure 5:
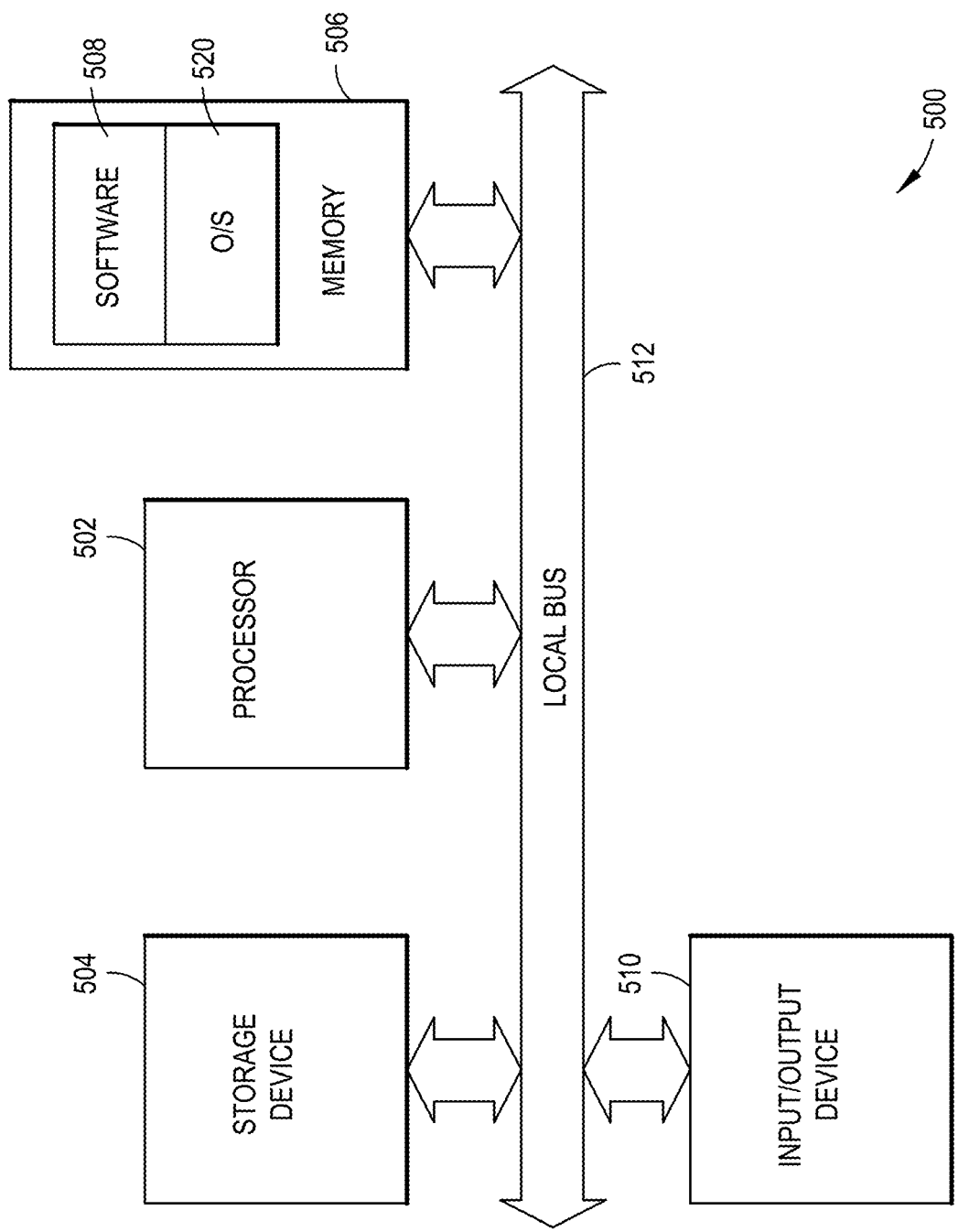
FIG. 5 is a schematic diagram illustrating an example of a system for executing functionality of the present invention.

The present system for executing the functionality described in detail above may include a computer, an example of which is shown in the schematic diagram of FIG. 5. The system 500 contains a processor 502, a storage device 504, a memory 506 having software 508 stored therein that defines the abovementioned functionality, input and output (I/O) devices 510 (or peripherals), and a local bus, or local interface 512 allowing for communication within the system 500. The local interface 512 can be, for example but not limited to, one or more buses or other wired or wireless connections, as is known in the art. The local interface 512 may have additional elements, which are omitted for simplicity, such as controllers, buffers (caches), drivers, repeaters, and receivers, to enable communications. Further, the local interface 512 may include address, control, and/or data connections to enable appropriate communications among the aforementioned components.

The processor 502 is a hardware device for executing software, particularly that stored in the memory 506. The processor 502 can be any custom made or commercially available single core or multi-core processor, a central processing unit (CPU), an auxiliary processor among several processors associated with the present system 500, a semiconductor based microprocessor (in the form of a microchip or chip set), a macroprocessor, or generally any device for executing software instructions.

The memory 506 can include any one or combination of volatile memory elements (e.g., random access memory (RAM, such as DRAM, SRAM, SDRAM, etc.)) and nonvolatile memory elements (e.g., ROM, hard drive, tape, CDROM, etc.). Moreover, the memory 506 may incorporate electronic, magnetic, optical, and/or other types of storage media. Note that the memory 506 can have a distributed architecture, where various components are situated remotely from one another, but can be accessed by the processor 502.

The software 508 defines functionality performed by the system 500, in accordance with the present invention. The software 508 in the memory 506 may include one or more separate programs, each of which contains an ordered listing of executable instructions for implementing logical functions of the system 500, as described below. The memory 506 may contain an operating system (O/S) 520. The operating system essentially controls the execution of programs within the system 500 and provides scheduling, input-output control, file and data management, memory management, and communication control and related services.

The I/O devices 510 may include input devices, for example but not limited to, a keyboard, mouse, scanner, microphone, etc. Furthermore, the I/O devices 510 may also include output devices, for example but not limited to, a printer, display, etc. Finally, the I/O devices 510 may further include devices that communicate via both inputs and outputs, for instance but not limited to, a modulator/demodulator (modem; for accessing another device, system, or network), a radio frequency (RF) or other transceiver, a telephonic interface, a bridge, a router, or other device.

When the system 500 is in operation, the processor 502 is configured to execute the software 508 stored within the memory 506, to communicate data to and from the memory 506, and to generally control operations of the system 500 pursuant to the software 508, as explained above.

When the functionality of the system 500 is in operation, the processor 502 is configured to execute the software 508 stored within the memory 506, to communicate data to and from the memory 506, and to generally control operations of the system 500 pursuant to the software 508. The operating system 520 is read by the processor 502, perhaps buffered within the processor 502, and then executed.

When the system 500 is implemented in software 508, it should be noted that instructions for implementing the system 500 can be stored on any computer-readable medium for use by or in connection with any computer-related device, system, or method. Such a computer-readable medium may, in some embodiments, correspond to either or both the memory 506 or the storage device 504. In the context of this document, a computer-readable medium is an electronic, magnetic, optical, or other physical device or means that can contain or store a computer program for use by or in connection with a computer-related device, system, or method. Instructions for implementing the system can be embodied in any computer-readable medium for use by or in connection with the processor or other such instruction execution system, apparatus, or device. Although the processor 502 has been mentioned by way of example, such instruction execution system, apparatus, or device may, in some embodiments, be any computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the processor or other such instruction execution system, apparatus, or device.

Such a computer-readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

In an alternative embodiment, where the system 500 is implemented in hardware, the system 500 can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Figure 7:
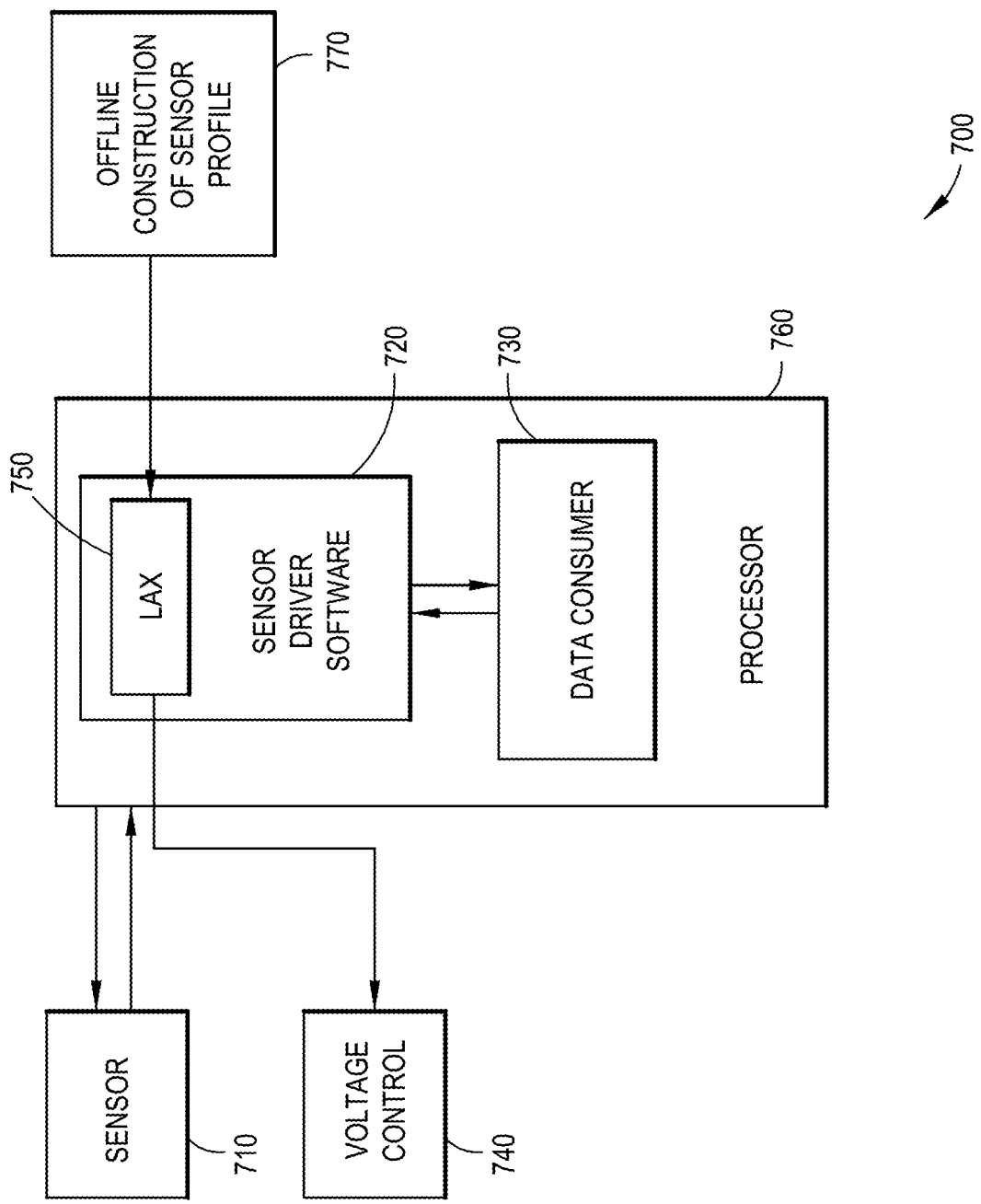
FIG. 7 is a block diagram of a second embodiment of a system for reducing energy used by sensors while at the same time tolerating deviations in sensor data.

Other implementations are also possible. FIG. 7 is a block diagram of a second embodiment of a system 700 for tolerating deviations in sensor data where Lax 750 is implemented as a portion of sensor driver software 720 resident on a host processor 760. The sensor driver software 720 exchanges data with a data consumer 730, which under the second embodiment is another process under the host processor 760. The sensor 710 is external to the host processor 760, as is a voltage control 740 that may be controlled via Lax 750. Lax 750 may be configured by an external offline construction of a sensor profile 770.

Figure 8:
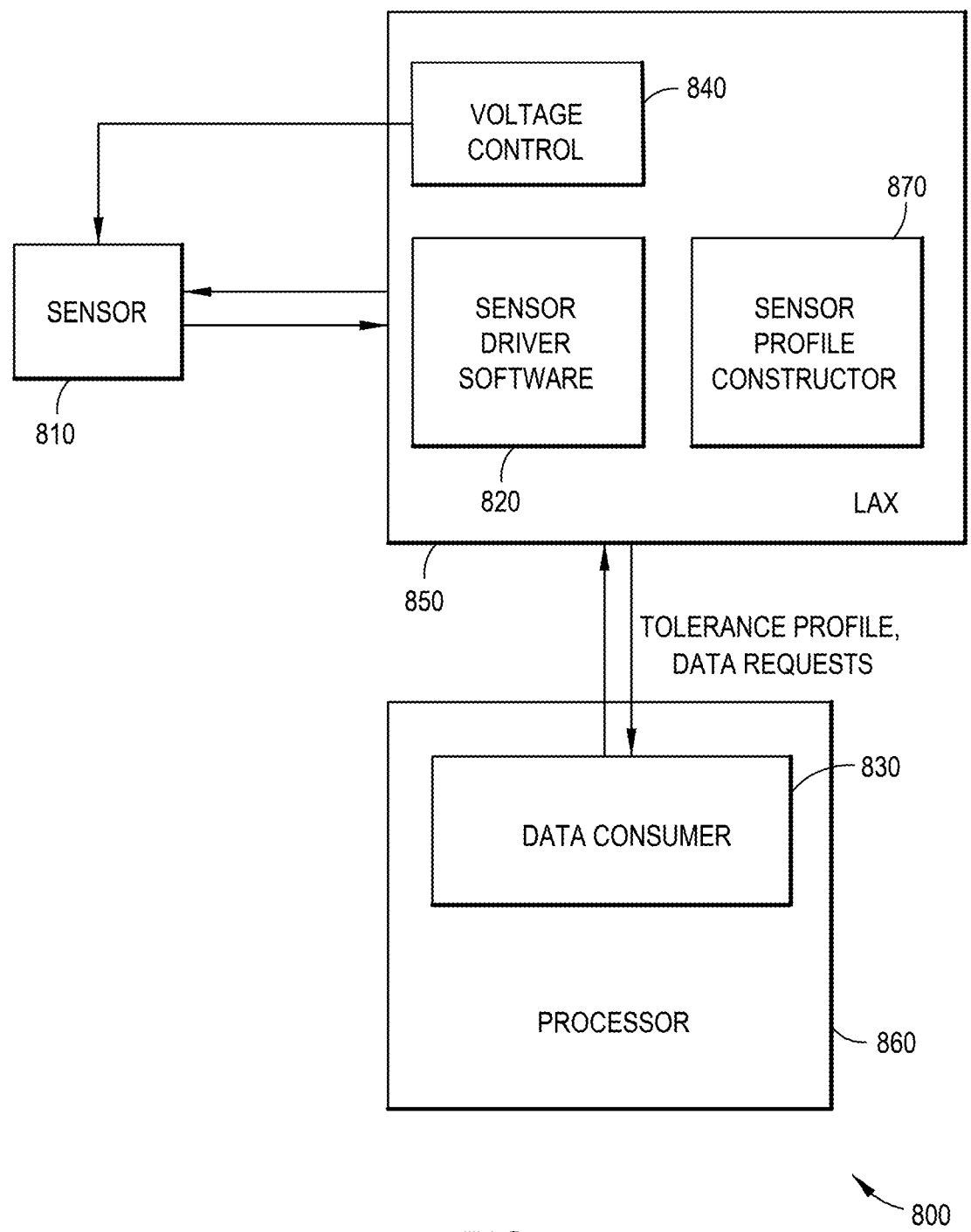
FIG. 8 is a block diagram of a third embodiment of a system for reducing energy used by sensors while at the same time tolerating deviations in sensor data.

FIG. 8 is a block diagram of a third embodiment of a system 800 for tolerating deviations in sensor data where Lax 850 is implemented apart from a processor 860 hosting a data consumer 830 in communication with Lax 850. The processor 860 exchanges information with Lax 850, for example, but not limited to a tolerance profile for the sensor 810 and data requests. The sensor driver software 820 may be hosted by Lax 850. The sensor 810 may be external to both Lax 850 and the processor 860, and the voltage control 840 that may be controlled via Lax 850 is incorporated into Lax 850. In contrast to the second embodiment 700, under the third embodiment a sensor profile constructor 870 may be integral to Lax 850.

In summary, the energy efficiency of many embedded sensor applications may be improved by driving the electrical interfaces of sensors in a manner that makes them use significantly less power, but at the cost of unreliable data acquisition. Lax lets systems programmers exploit this insight in a controlled manner.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A system for providing sensor data to a sensor data consumer comprising:
    a sensor configured to produce the sensor data; and
    a facility comprising a processor and a memory configured to store non-transient instructions, which when executed by the processor performs the steps of:
        receiving a sensor profile of the sensor indicating a relationship between a sensor parameter operating range and a resulting deviation of the sensor data;
        receiving a tolerance profile of the sensor data consumer indicating a tolerable degree of deviation of the sensor data; and
        scaling a parameter of the sensor according to the tolerance profile,
    wherein said scaling reduces a power dissipation level of the sensor, and wherein said deviation comprises a difference between data output by the sensor with and without scaling the parameter.

2. The system of claim 1, further comprising a sensor driver in communication with the sensor and configured to receive the sensor data and/or to control operation of the sensor, wherein the sensor driver is in communication with the facility and configured to control the sensor according to facility data received from the facility.

3. The system of claim 1, wherein the tolerance profile comprises one of the group consisting of a latency tolerance, a loss or throughput tolerance, an offset value, and a value deviation tolerance.

4. The system of claim 1, wherein scaling the parameter of the sensor further comprises changing a timing of when the sensor produces sensor data.

5. The system of claim 1, wherein scaling the parameter of the sensor further comprises changing a timing of when the sensor produces sensor data.

6. The system of claim 1, wherein scaling the parameter of the sensor further comprises changing a power parameter of the sensor.

7. The system of claim 6, further comprising a voltage regulator, and wherein scaling the power parameter of the sensor comprises changing a voltage level provided to the sensor.

8. The system of claim 6, further comprising the step of determining a tolerable degree of deviation in the sensor data resulting from changing the power parameter of the sensor.

9. The system of claim 8, wherein an amount of the scaling of the power parameter is informed by the tolerable degree of deviation in the sensor data.

10. The system of claim 2, further comprising an operating system operating in conjunction with the sensor driver and the facility.

11. The system of claim 1, wherein the facility is configured to access the sensor data.

12. The system of claim 11, wherein the processor further performs the steps of defining the tolerance profile and/or the sensor profile.

13. The system of claim 12, wherein the facility is configured to define the tolerance profile based at least partially on needs of the sensor data consumer and/or the sensor profile.

14. A device in communication with a sensor configured to produce sensor data and provide sensor data to a sensor data consumer comprising:
   a processor and a memory configured to store non-transient instructions, which when executed by the processor performs the steps of:
      receiving a sensor profile of the sensor indicating relationship between a sensor parameter operating range and a resulting deviation of the sensor data;
      receiving a tolerance profile of the sensor data consumer indicating a tolerable degree of deviation of the sensor data; and
      scaling a parameter of the sensor and/or a sensor power supply according to the tolerance profile,
   wherein said scaling reduces a power dissipation level of the sensor, and wherein said deviation comprises a difference between data output by the sensor with and without scaling the parameter.

15. The device of claim 14, further comprising a sensor driver in communication with the sensor and configured to receive the sensor data and/or to control operation of the sensor, wherein the sensor driver is in communication with the facility and configured to control the sensor according to facility data received from the facility.

16. A method to be executed by a processor configured to execute non-transitory instructions stored in a memory to perform the steps of:
   accessing a sensor profile of the sensor indicating a relationship between a sensor parameter operating range and a resulting deviation of the sensor data;
   accessing a tolerance profile of a sensor data consumer indicating a tolerable degree of deviation of sensor data accessible to the sensor data consumer;
   providing the tolerance profile to a facility in communication with a sensor driver configured to control the sensor; and
   scaling a parameter of the sensor according to the tolerance profile to reduce a power dissipation level of the sensor,
   wherein said deviation comprises a difference between data output by the sensor with and without scaling the parameter.

17. The method of claim 16, further comprising the step of defining the sensor profile and/or the tolerance profile.

* * * * *